United States Patent [19]

Lesho et al.

[11] Patent Number: 4,844,076

[45] Date of Patent: Jul. 4, 1989

[54] INGESTIBLE SIZE CONTINUOUSLY TRANSMITTING TEMPERATURE MONITORING PILL

[75] Inventors: Jeffery C. Lesho, Brookeville; Arthur F. Hogrefe, Laurel, both of Md.

[73] Assignee: The Johns Hopkins University, Baltimore, Md.

[21] Appl. No.: 236,885

[22] Filed: Aug. 26, 1988

[51] Int. Cl.$^4$ ................................................. A61B 5/07
[52] U.S. Cl. ..................................... 128/631; 128/736; 128/903
[58] Field of Search ................. 128/736, 631, 903; 340/870.17, 573; 331/66

[56] References Cited

U.S. PATENT DOCUMENTS

| | | | |
|---|---|---|---|
| 3,739,279 | 6/1973 | Hollis | 128/631 |
| 3,971,362 | 7/1976 | Pope et al. | 128/631 |
| 4,689,621 | 8/1987 | Kleinberg | 128/736 |

OTHER PUBLICATIONS

Crystal-Controlled, Surgically Implantable Temperature Telemetry Transmitter, J. L. Riley, Medical & Biological Eng. & Comp., May 1980, pp. 363–364.

Primary Examiner—Lee S. Cohen
Assistant Examiner—Scott Getzow
Attorney, Agent, or Firm—Robert E. Archibald; Howard W. Califano

[57] ABSTRACT

A temperature responsive transmitter is disclosed. The transmitter utilizes a unique circuit design that allows encapsulation in an ingestible size capsule. The inventive circuit design uses a one transistor inverting amplifier with a tank circuit forming the link between the transistor's collector and the battery. The tank circuit is tuned to provide a lagging capacitive load which causes the inverting amplifier to oscillate. The tank circuit contains a coil inductor that emits a near field magnetic communications field containing temperature information. The ingestible size temperature pill can be configured in a rechargeable embodiment. In this embodiment the pill uses the inductive coil in the tank circuit as the magnetic pickup to charge a rechargeable nickel cadmium battery.

17 Claims, 3 Drawing Sheets

INGESTIBLE SIZE CONTINUOUSLY TRANSMITTING TEMPERATURE MONITORING PILL

STATEMENT OF GOVERNMENTAL INTEREST

The Government has rights in this invention pursuant to Contract No. N00039-87-C-5301 awarded by the Department of the Navy.

BACKGROUND OF THE INVENTION

1. Field of the Invention

The invention relates to a miniature temperature responsive transmitter that is capable of being encapsulated within an ingestible size capsule.

2. Description of Prior Art

The body core temperature can be accurately measured in only a few locations without implanting a sensor into the body. Most commonly, a rectal thermometer is used for core temperature measurement. However, this method is inconvenient and inaccurate in many applications. The oral temperature, which is also frequently used, is a quite unreliable measure of core temperature because of variations due to breathing and to ingesting hot and cold liquids and solids. However, an ingestible pill that would enter the digestive system would provide the most accurate means of body core temperature measurement.

Various attempts have been made to produce an ingestible size temperature pill. U.S. Pat. No. 4,689,621 issued to Kleinburg discloses an ingestible size transmitter using a unique circuit having two identically biased transistors that are connected at their base, collector and emitter. U.S. Pat. No. 3,893,111 issued to John C. Cotter describes a temperature capsule to be used with larger animals to monitor their temperatures.

However, the prior art temperature capsules contain circuit designs that require a large number of components and larger batteries that results in a capsule too large to be conveniently ingested by a patient.

SUMMARY OF THE INVENTION

The present invention is a temperature responsive transmitter that is capable of being encapsulated within an ingestible size pill. The unique circuit configuration uses a reduced number of components and allows the transmitter to operate with a small single cell battery that supplies 1.0 to 1.5 volts. The invention includes the following components: a battery; an inverting amplifier; a temperature sensitive crystal; and, a tank circuit that is operably coupled between the output of the inverting amplifier and the battery and tuned to a frequency lower than the natural frequency of the temperature sensitive crystal. The tank circuit positioned in this configuration provides both a lagging phase at the output of the inverter amplifier and a coil to emit a near field magnetic communication signal haveing a frequency dependent upon the temperature sensitive crystal, which is itself temperature dependent. The miniature sized transmitter/oscillator is able to function because of the phase lag provided by the tank circuit. Tuning the tank circuit to a frequency lower than the natural frequency of the temperature sensitive crystal allows the tank circuit to provide a capacitive load, i.e., a phase lagging load, which is necessary for the inverter to oscillate.

A second embodiment of the invention includes a rechargeable battery and a miniaturized charging circuit: The battery is charged from a remotely generated magnetic field. In this embodiment the ingestible pill would be charged prior to use by the patient, thus providing an extremely long shelf life for the ingestible pill.

A first novel feature of the invention is the use of a tank circuit that is connected to an inverter amplifier and tuned to a frequency that is lower than the natural frequency of the temperature sensitive crystal oscillator. This feature allows the tank circuit to provide a phase lag the output of the inverter amplifier, while still providing the large circulation current needed to generate a communications field.

A second novel feature is the unique placement of the tank circuit in association with the inverter amplifier so that it acts as a voltage doubler and provides twice the battery voltage across the tank coil. Since the tank coil emits the communication field this allows a maximum transmission signal with minimum voltage.

A third novel feature is a use of a tank circuit to provide a high A.C. impedance between the battery and the collector of the transistor amplifier so that the transistor amplifier can be biased with no D.C. load drop.

A fourth novel feature is a use of the features described above so that a miniaturized transmitter can operate from a single cell battery providing 1.0 to 1.5 volts.

A fifth novel feature is a unique charging configuration that allows the ingestible size pill to contain both a transmitter circuit and a recharging circuit. In particular, the circuit uniquely reduces component requirements by using the tank circuit to perform the following multiple functions: (1) provide a lagging load for the oscillator circuit; (2) stimulate the communication signal, and (3) act as a receptor in the recharging circuit.

A sixth novel feature is the multiple layer configuration of the coil. The electronics is encapsulated in a first cylindrical shape of epoxy with the coil wrapped around a portion of this first cylindrical shape (but, not around the battery). The first cylindrical shape and the coil are then encapsulated by a second epoxy layer and an outer biocompatible layer.

DETAILED DESCRIPTION OF THE PREFERRED EMBODIMENT

Figure 1:
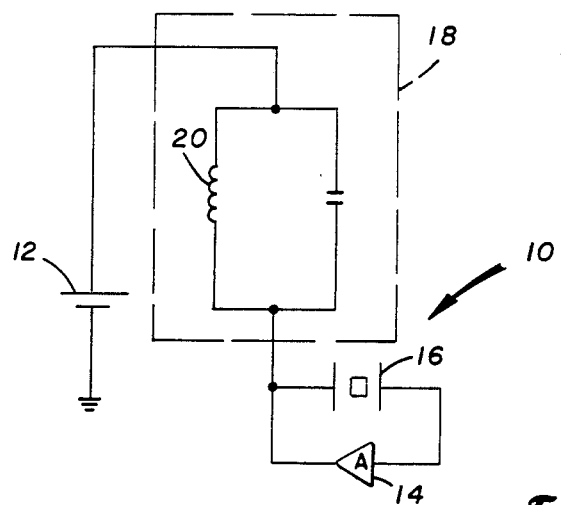
FIG. 1 is a schematic drawing of the present invention using an inverting amplifier.

The schematic drawing for the first embodiment of the temperature responsive transmitter 10 is shown in FIG. 1. The transmitter includes: a battery 12; an inverting amplifier 14; that is operably biased to the battery; a temperature sensitive crystal 16 operably coupled between the input and output of the inverting amplifier 14;

and, a tank circuit 18 operably coupled between the output of the inverting amplifier 14 and the battery 12. The temperature sensitive crystal 16 has a natural frequency dependent on local temperature. Applicants have chosen a miniature tuning fork manufactured by Statek Corp. as the temperature sensitive crystal that operates in a Pierce oscillator configuration. The battery 12 can be a single cell battery generating between 1-2 volts; Applicants have selected a nickel cadmium battery, although other miniature low voltage batteries would work equally well.

As shown in FIG. 1, the tank circuit 18 performs a dual function. First, the tank circuit is tuned to a frequency lower than the natural frequency of the temperature sensitive crystal 16 to provide a lagging phase shift at the output of the inverting amplifier 14. (This feature is essential for the inverting amplifier to operate as an oscillator in this low voltage, minimum component design.) Secondly, the tank circuit contains an inductive coil 20 used to emit a near field magnetic signal. The frequency of the near field emission is dependent on the frequency of the temperature sensitive crystal which is itself temperature dependent. The inductive coil is 300 turns of No. 40 wire wound around the potted circuitry (about a 0.3" diameter) and offset from the battery by at least ⅛". The inductive coil is nominally about 0.62 mH, with a resistive load of about 55 Ohms.

Figure 2:
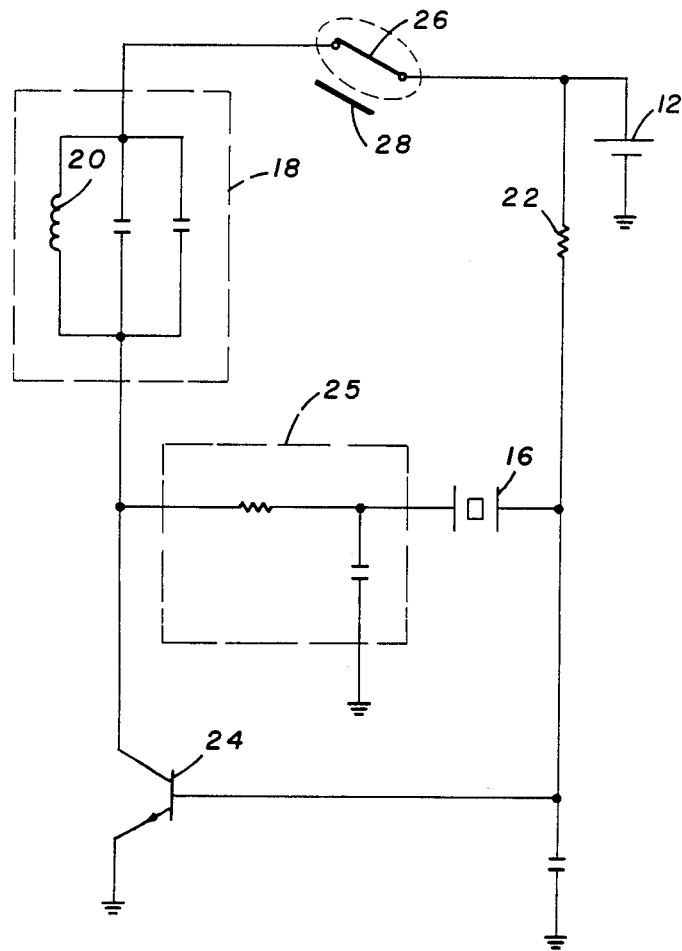
FIG. 2 is a schematic diagram of the present invention in which the inverting amplifier is a single transistor amplifier.

In FIG. 2, a single transistor amplifier 24 is configured as the inverting amplifier (element 14 of FIG. 1). The base of the transistor is connected to the battery through a biasing resistor 22. The temperature sensitive crystal and RC network 24 is placed within the connector-base circuit. The combined phase lag produced by tank circuit 18, temperature sensitive crystal 16, and RC network 25 is needed to produce oscillation in the transistor amplifier 24. The RC network provides an additional phase lag in the collector-base circuit that may be necessary for the transistor amplifier to operate as an oscillator.

There are several advantages derived from the placement of the tank circuit on the collector of transistor 24. First, the tank circuit is tuned to a frequency lower than the natural frequency of the temperature sensitive crystal 16 to provide a lagging phase shift in the collector-base circuit of the transistor amplifier 24. Secondly, the tank circuit contains an inductive coil 20 used to emit a near field magnetic signal. Thirdly, the tank circuit provides a large circulating current through inductive coil 20; the tank circuit acts as a voltage doubler thereby optimizing the signal emitted by the coil to the battery drain by storing voltage in the tank circuit. (The tank circuit results in twice the battery voltage appearing at the transistor 24 collector.) Fourthly, because the tank circuit provides a high impedance between the battery and the collector of the transistor 24, only a single $V_{be}$ drop across the transistor is necessary for proper biasing - therefore, a lower voltage single cell battery can be used.

The transmitter in FIG. 2 does not have a rechargeable power source. Therefore, a reed switch 26 biased closed by a magnet 28 is used to disconnect the battery from the circuit during storage. To accomplish this, the pill is stored in an externally supplied magnetic field which overrides the magnetic field produced by magnet 28 and causes the reed switch 25 to be opened; thus, disconnecting the battery 12 from the transmitting circuit and preserving battery life during storage.

Figure 3:
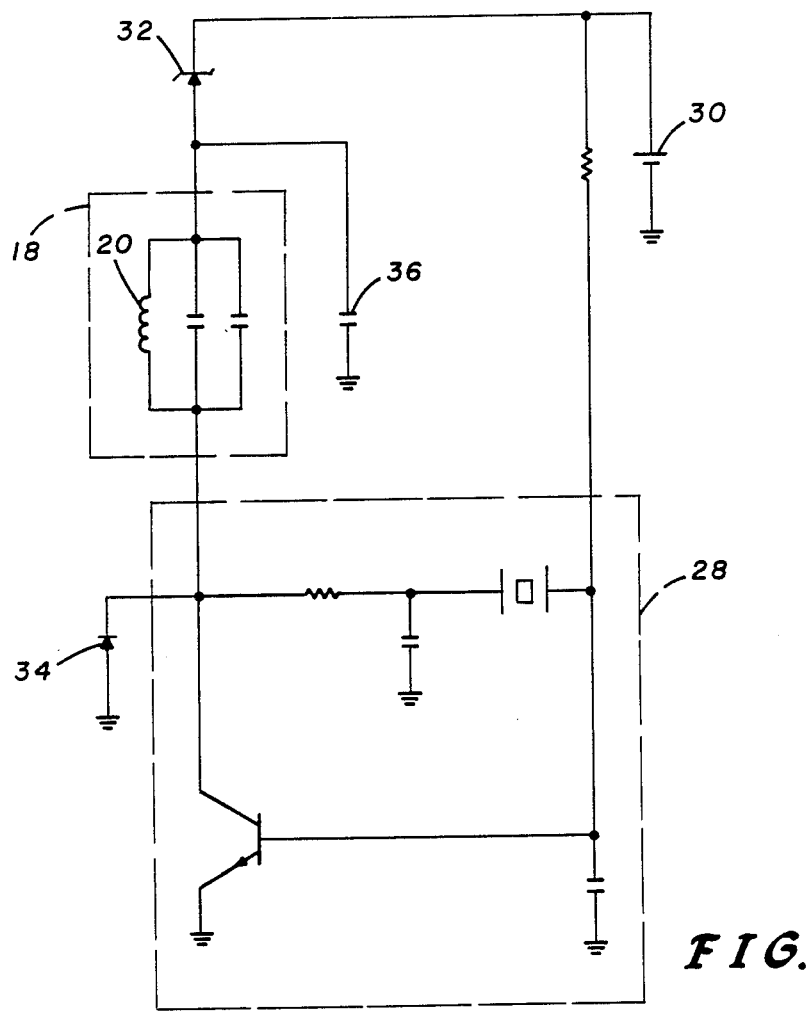
FIG. 3 is a second embodiment of the present invention containing a recharging circuit.

FIG. 3 is a schematic diagram of an alternative embodiment of the temperature responsive transmitter. The oscillator 28 and tank circuit 18 are similar to those appearing in FIG. 2; however, this circuit includes a rechargeable battery 30 with a circuit capable of charging the battery from an externally supplied magnetic field. The charging operation occurs when the pill is inserted into another coil having a magnetic flux of sufficient density and frequency. A 1 mA regulated charge rate is desired to recharge a nickel cadmium battery in a minimum time without causing damage to the chemical system. The inductive coil 20 (which now acts in a dual capacity as a magnetic pickup coil) connects to the rechargeable battery 30 through a current limiter 32. Applicants have selected a JFET that causes current limiting only when the voltage of the coil is more positive than the battery (about 2 Volts more positive for the full limited current output). Charging occurs when an external field generates a voltage across the inductor coil 20 greater than the battery potential. A rectifier 34 converts the sine wave picked up by the inductor 20 into a half wave charging current. The rectified signal drives a storage capacitor 36 which in turn charges the battery 30 through the current limiter 32.

Figure 4:
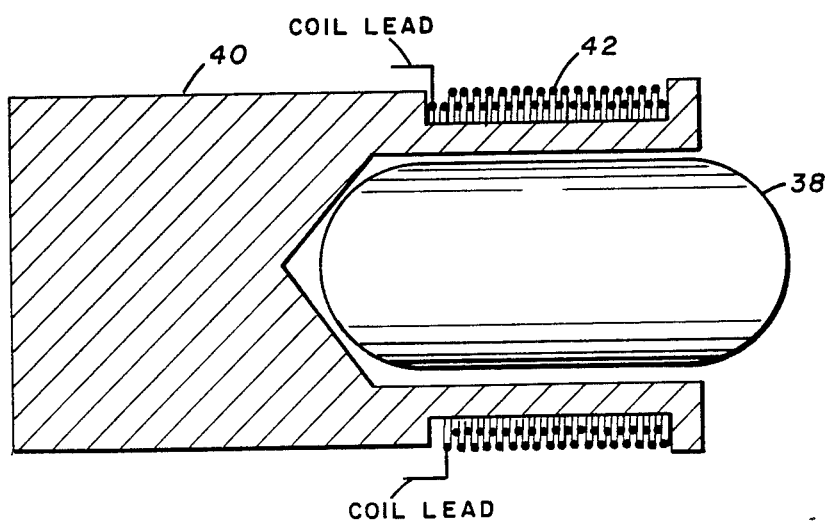
FIG. 4 is an enlarged cross-sectional view of the pill inserted into the charger form for recharging.

FIG. 4 is a cross-sectional view of the charger mechanism. The pill 38, containing the temperature responsive transmitter with the recharging circuitry, is inserted into a charger form 40. Coil 42 generates an oscillating magnetic field that couples into the pill's inductive coil (not shown) and recharges the pill's battery.

Figure 5:
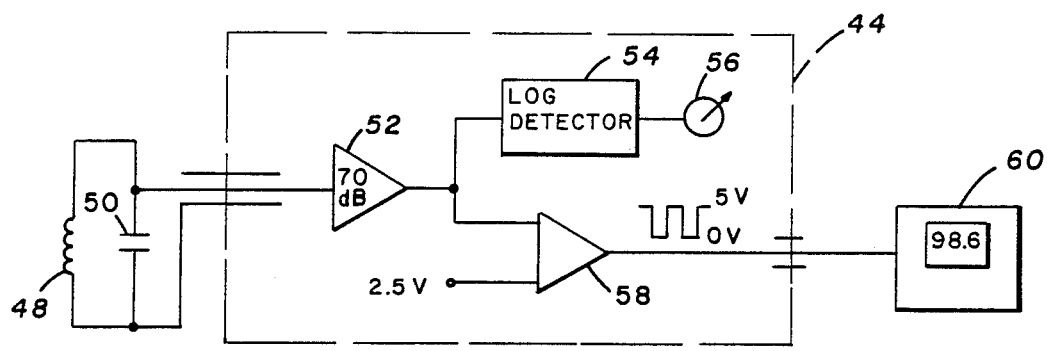
FIG. 5 is a block diagram of the receiver circuit used with the temperature sensing pill.

FIG. 5 is a block diagram of the receiver used to pick up the signal transmitted by the temperature responsive pill. The receiver can be used with the transmitter embodiment shown in FIGS. 1-3. The external pill receiver 44 is used to drive a frequency counter 60 and a field strength meter 56 to provide the operator with a signal strength indication. The pickup coil 48 is used to couple the inductive coil in the pill's transmitter. The Applicants have used two external pickup coil configurations; one is 5 centimeters in diameter, and the other is 23 centimeters in diameter. The small coil is easily placed in a person's garment or taped to the skin without interfering with movement and allowing for easier location of the pill within the digestive system. The larger coil can be used when a person cannot wear a coil. This coil may be mounted on the side of the bed or in a mattress cover. The coil is further from the pill and must be larger to pick up the inductive signal.

The external coil 48 is either tuned or untuned. If a tuning capacitor 50 is used, it is placed on the coil so that the same receiver can be used with any coil. The voltage across the external coil is amplified by a field effect transistor amplifier 52. The gain of the amplifier is approximately 70 dB, and this gain provides a pickup range of 25 cms. The frequency of the amplified signal is the same as the frequency telemetered by the pill and therefore contains the information needed to measure temperature. The amplifier 52 drives a log detector 54 which is connected to a field strength meter 56. The field strength meter 56 is used by the operator to assure than an adequate link is established between the pill and the remote receiver. The amplifier 52 also drives ta comparator 58. The digital output from the comparator is coupled to a frequency counter 60, or a personal computer which counts the frequency of the emitted signal and performs the calculation to display the temperature sensed by the pill.

Figure 6:
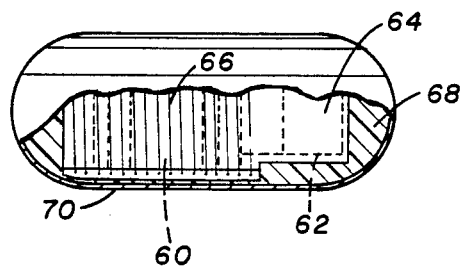
FIG. 6 is a cross-sectional view showing the multiple layer pill configuration.
Figure 7:
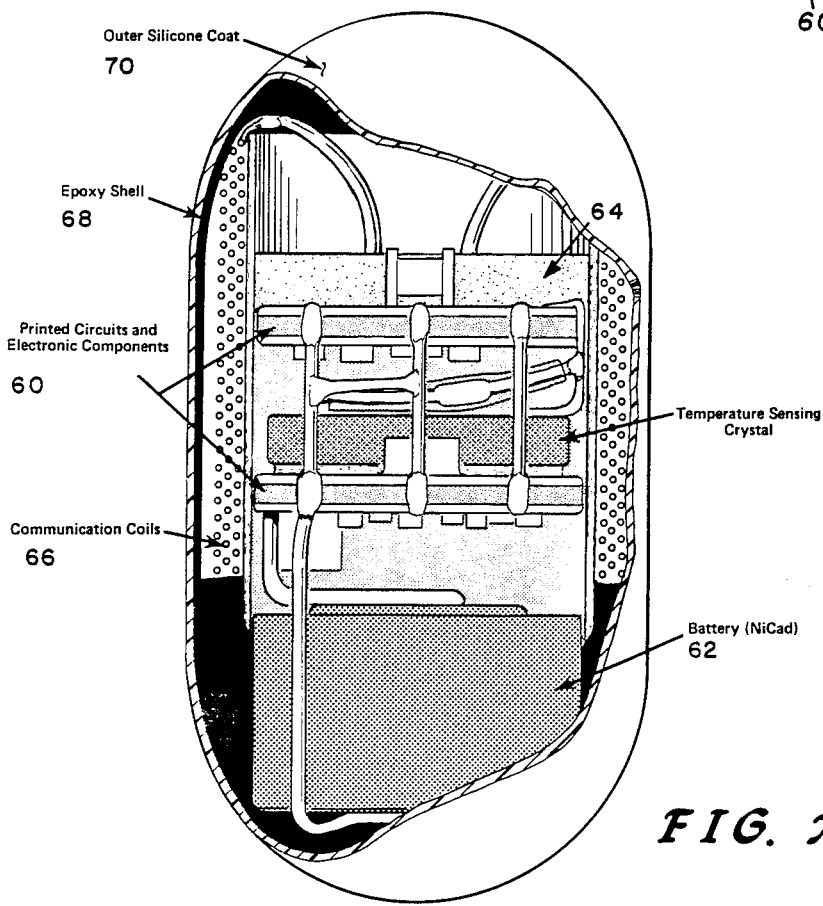
FIG. 7 is a cut-away view showing inner layers of the pill configuration.

FIG. 6 shows a schematic view and FIG. 7 shows a cutaway view of the temperature pill. These figures will be referred to when discussing the method of fabrication. The electronics are fabricated onto a printed circuit board 60 that is operably connected above the small battery 62. The next fabrication step is to pot the pill with epoxy. This fills in the electronics, stabilizes the circuit and forms a cylindrical block of epoxy 64 around which the induction coil 66 can be subsequently wound. All leads are removed except for those leads attached to the inductive coil and the tuning capacitor. A 300-turn coil 66 is wrapped around the epoxy cylinder; however, the coil is kept away from the battery as much as possible (i.e., the coil is only wrapped around the circuit components and not the battery). The tuning capacitor is then selected and soldered in place. A second epoxy layer 68 is then applied which holds the inductive coil in place, provides extra protection for the electronics and gives the pill the familiar capsule-like shape. The next outer biocompatible layer 70 must then be added to the pill. The outer layer of the pill must be resistive to degradation by the contents of digestive tract as well as biocompatible. For this layer, silicone was selected. The pills were encapsulated in silicone rubber by dipping them into a solution in which silicone rubber is dispersed in cyclohexene. The cyclohexene evaporates depositing the silicone rubber. Applicants have found that three such dippings are necessary to obtain the desired 0.5 millimeter coating on the pill.

When used to detect core body temperature, the temperature responsive pill would first be either recharged prior to use (for the FIG. 3 embodiment), or removed from an external magnetic field so as to allow the reed switch (see FIG. 2) to close and connect the battery to the transmitter. The pill would then either be swallowed, or inserted into the vagina, anus or other body cavity of the patient. The external receiving coil would then be positioned and the external receiver would pick up the signal transmitter by the pill and display the patient's core temperature. The present miniaturized transmitter can also be used for non-medical use, such as industry quality control.

Obviously many modifications and variations of the present invention are possible in light of the above teachings. It is, therefore, to be understood that within the scope of the appended claims, the invention may be practiced otherwise than as specifically described.

What is claimed is:

1. A miniaturized temperature responsive transmitter comprising:
   a battery providing a voltage $V_b$;
   reed-switch means adapted to be controlled by a magnet to disconnect the battery during storage;
   a one-transistor inverting amplifier having an input and output and operably biased to said battery;
   a temperature-sensitive crystal operably coupled between said input and output of said inverting amplifier and having a natural frequency dependent on local temperature;
   a tank circuit having an inductor and a capacitor, operably coupled between said output of said inverting amplifier and said battery and tuned to a frequency lower than the natural frequency of said temperature-sensitive crystal for both providing a lagging phase shift at the output of said inverting amplifier and for emitting a near field magnetic signal from said inductor, wherein the frequency of said near field magnetic signal is dependent upon the frequency of the temperature sensitive crystal which is temperature dependent, and wherein said inverting amplifier acts as a switch causing said capacitor to charge and discharge through said inductor, thereby allowing the tank circuit to operate at 2 $V_b$ peak-to-peak volts.

2. The apparatus of claim 1, wherein said tank circuit is connected between the collector of said transistor amplifier and said battery, and said temperature sensitive crystal is connected in the collector/base circuit of the one-transistor amplifier.

3. The apparatus of claim 2, wherein said battery is a one-cell battery.

4. The apparatus of claim 2, wherein said temperature sensitive crystal is operating in a Pierce oscillator configuration.

5. The apparatus of claim 2, wherein a separate RC network is connected to the collector/base circuit of the one transistor amplifier to provide an additional lagging phase shift.

6. The apparatus of claim 3, wherein said battery is a nickel cadmium battery.

7. A rechargeable, miniaturized temperature responsive transmitter comprising:
   a rechargeable battery;
   an inverting amplifier having an input and output and operably biased to said battery;
   a temperature sensitive crystal operably coupled between said input and output of said inverting amplifier and having a natural frequency dependent on local temperature;
   a tank circuit having a first and second terminal with an inductive coil connected therebetween, the first terminal of said tank circuit being connected to said inverting amplifier;
   a current limiting device connecting said second terminal of said tank circuit to said battery, for limiting the current that can flow into said rechargeable battery;
   a charging capacitor connected between said second terminal of said tank circuit and ground for storing electrical energy picked up by said inductor;
   a diode connected between said first terminal of said tank circuit and said ground for rectifying full wave oscillation picked up on the inductor and for charging said charging capacitor; and,
   wherein said tank circuit is tuned to a frequency lower than the natural frequency of said temperature sensitive crystal, and wherein said tank circuit performs the following functions:
   i. providing a lagging phase shift at the output of said inverting amplifier;
   ii. emitting a near field magnetic signal from said inductor at a frequency dependent on the temperature sensitive crystal which is temperature dependent; and,
   iii. a power pickup used to recharge the rechargeable battery.

8. The apparatus of claim 7, wherein said inverting amplifier is a one transistor amplifier with said tank circuit connected between the collector of said transistor amplifier and said rechargeable battery and said temperature sensitive crystal is connected in the collector/base circuit of said one-transistor amplifier.

9. The apparatus of claim 8, wherein said battery is a onecell battery.

10. The apparatus of claim 8, wherein said battery is a rechargeable nickel cadmium battery.

11. The apparatus of claim 8, wherein said temperature sensitive crystal is operating in a Pierce oscillator configuration.

12. The apparatus of claim 8, wherein a separate RC network is connected in the collector/base circuit of the one transistor amplifier to provide an additional lagging phase shift.

13. The apparatus of claim 8, wherein said current limiting device is a JFET that causes current limiting only when the voltage of the inductive coil is more positive than the rechargeable battery.

14. An ingestible temperature sensing pill comprising:
a first cylinder of epoxy encompassing a battery and a transmitter/sensitive circuit, said transmitting/sensing circuit including:
an inverting amplifier having an input and output and powered by said battery;
a temperature sensitive crystal operably coupled between said input and output of said inverting amplifier and having a natural frequency dependent on local temperature,
a tank circuit having a coil inductor, operably coupled between said output of said inverting amplifier and said battery and tuned to a frequency lower than the natural frequency of said temperature sensitive crystal for both providing a lagging phase shift at the output of said inverting amplifier and for emitting a near field magnetic signal from said coil inductor, wherein the frequency of said near field magnetic signal is dependent upon the frequency of the temperature sensitive crystal which is frequency dependent,
wherein said coil inductor being wrapped around said first epoxy cylinder but not encompassing said battery;
a second epoxy shell encompassing said first cylinder of epoxy and said coil inductor, and,
an outer coating of biocompatible material covering said second epoxy shell.

15. The apparatus of claim 14, wherein said inverting amplifier is a one transistor amplifier with the tank circuit connected between the collector of said transistor amplifier and said battery and said temperature sensitive crystal is connected in the collector/base circuit of said one transistor amplifier.

16. The apparatus of claim 14, wherein said sensing pill is shaped to form an ingestible capsule.

17. The apparatus of claim 14, wherein said outer coating of biocompatible material is an outer coating of silicone rubber.

* * * * *